US006809207B2

(12) United States Patent
Alla et al.

(10) Patent No.: US 6,809,207 B2
(45) Date of Patent: Oct. 26, 2004

(54) AMINO ACID DERIVATIVES

(75) Inventors: Sekar Alla, Greensboro, NC (US); Seung-Yong Choi, Greensboro, NC (US); Dale Dhanoa, Wakefield, MA (US); Elso DiFranco, Greensboro, NC (US); Galina Krokhina, Greensboro, NC (US); Keqiang Li, Greensboro, NC (US); Balasubramanian Thiagarajan, Raleigh, NC (US); Wen-Chun Zhang, Greensboro, NC (US)

(73) Assignee: PharmaCore, Inc., High Point, NC (US)

( * ) Notice: Subject to any disclaimer, the term of this patent is extended or adjusted under 35 U.S.C. 154(b) by 0 days.

(21) Appl. No.: 10/202,137

(22) Filed: Jul. 24, 2002

(65) Prior Publication Data

US 2003/0064976 A1 Apr. 3, 2003

Related U.S. Application Data

(60) Provisional application No. 60/307,524, filed on Jul. 24, 2001.

(51) Int. Cl.$^7$ .............................................. C07D 335/02
(52) U.S. Cl. .............................. 549/28; 549/13; 549/58; 549/70; 549/74; 549/76; 549/426; 546/246; 546/247; 546/248; 546/335; 560/32; 560/37; 560/115; 562/418; 562/442; 562/507
(58) Field of Search ................................ 546/248, 335, 546/246, 247; 549/28, 70, 426, 74, 76, 58, 13; 560/37, 32, 115; 562/442, 418, 507; 514/315, 357, 432, 448, 538, 567

(56) References Cited

U.S. PATENT DOCUMENTS

| | | | |
|---|---|---|---|
| 4,535,167 A | 8/1985 | Freidinger et al. |
| 4,631,211 A | 12/1986 | Houghten |
| 4,757,153 A | 7/1988 | Hansen, Jr. et al. |
| 5,280,093 A | 1/1994 | Jacquier et al. |
| 5,883,077 A | 3/1999 | Brunck et al. |

FOREIGN PATENT DOCUMENTS

| | | | |
|---|---|---|---|
| EP | 1013769 | * | 6/2000 |
| GB | 1 353 493 A | | 5/1974 |

OTHER PUBLICATIONS

Cao, X et al., "Synthesis of NH–acyl–αaminoamides on rink resin: inhibitors of the hematopoietic protein tyrosine phosphatase" Bioorg. Med. Chem. Lett. vol. 5, 1995, 2953–2958.
Demharter, A. et al. Synthesis of a Chiral 1,1'—Iminodicarboxylic Acid Derivatives from—α Amino Acids Aldehydes, Isocyanides, and Alchohols by the Diastereoselective Five–Center–Four–Component Reactron. Angew. Chem. Int. Ed. Engl. 35: 173–175 (1996).

Faust, "Geminal Benzotriazolyl Ethoxy derivatives–Efficient auxiliaries in the synthesis of unsaturated carbonyl compounds", J. Prakt. Chem., 1997, vol. 339, p. 98–100.
Greene, T.W., "Protection of the Amino Group" Protective Groups in Organic Synthesis, John Wiley & Sons, New York, NY, Chapter 7 (1981).
Keating, et al., "Molecular diversity via a convertible isocyanide in the Ugi four component condensation" J. Am. Chem. Soc. 1995, vol. 117, 7842–7843.
Keating, T.A. et al. "Postcondensation Modifications of Ugi Four–Component Products: 1–Isocyanocyclohexene as a convertible Isocyanide Mechanism of Conversion, Synthesis of Diverse Structures, and Demonstration of Resin Capture" J. Am. Chem. Soc. 1996, vol. 118, p 2574–2583.
Kitaguchi et al."Enzymatic formation of an isopeptide bond involving the εamino group of lysine" Tetrahedron Lett., 1988, vol. 29, pp. 5487–5488.
Kunz, H. et al. "Carbohydrates as chiral templates: diastereoselective Ugi synthesis of (S) amino acids using o–acylated d–arabinopyranosylamine as the auxiliary" Tetrahedron . Lett., 1989, vol. 30, pp. 4109–4110.
Linderman, "Enhanced diastereoselectivity in the asymmetric Ugi reaction using a new convertible isonitrile" J. Org. Chem., 1999, vol. 64, pp. 336–337.
Mjalli, et al., "Solid phase synthesis of pyrroles derived from a four component condensation" Tetrahedron Lett., 1996, vol. 37, pp. 2943–2946.
Sigmüller et al. "Chiral ferrocenylalkylamines from (–)–menthone" Tetrahedron, 1986, vol. 42, pp. 5931–5940.
Ugi, I., Isonitrile Chemistry, p. 1, Academic Press, New York and London, 1971.
Ugi, I., "From Isocyanides via four–component condensations to antibiotic synthesis" Angew Chem., Int. Ed. Engl., 1982, vol. 21, pp. 810–819.
Ugi, I., "Perspektiven von Multikomponentenreaktionen und deren Bibliotheken" J. Prakt. Chem., 1997, vol., 339, p. 499–516.
International Search Report for related PCT application US 02/23336 mailed Dec. 23, 2002.
English Translation of pp. 502 and 504 of Ugi, I., "Perspektiven von Multikomponentenreaktionen und deren Bibliotheken" J. Prakt. Chem., 1997, vol., 339, pp. 499–516.
Domling et al, "Multicomponent Reactions with Isocyanidas." Angew. Chem. Int. Ed., 2000, vol. 39, pp. 3168–3210.

* cited by examiner

Primary Examiner—Shailendra Kumar
(74) Attorney, Agent, or Firm—Kirkpatrick Stockton LLP

(57) ABSTRACT

The present invention provides certain alpha-amino acids and derivatives thereof, such as, but not limited to, esters, amides and salts. These derivatives may comprise such representative side groups as a phenyl, pyridyl, piperidinyl, tetrahydropyranyl, tetrahydrothiopyranyl, or thienyl group. The present invention further provides a method for synthesizing alpha-amino acids and derivatives thereof via a modified Ugi type reaction using an aldehyde, ammonium formate and a $C_1$–$C_5$ alkyl isocyanide. The compounds provided by this method are useful in the development of new pharmaceuticals for the treatment of human diseases.

14 Claims, No Drawings

AMINO ACID DERIVATIVES

STATEMENT OF RELATED APPLICATION

The present application claims priority under 35 USC 119 from U.S. Provisional Application Ser. No. 60/307,524, filed Jul. 24, 2001, entitled "Amino Acid Derivatives," the disclosure of which is incorporated herein by reference.

FIELD OF THE INVENTION

This invention relates to certain alpha-amino acetic acids and derivatives thereof, such as, but not limited to, esters, amides and salts. This invention also relates to methods to synthesize these alpha-amino acids.

BACKGROUND OF THE INVENTION

Amino acid derivatives have applications in the manufacture of a wide range of pharmaceutical products and therapeutic agents used for the treatment of human disease. For example, amino acid derivatives have been used in the development of peptide and non-peptide based drugs, including HIV protease inhibitors for the treatment of AIDS, and the anti-cancer drug Abrelix, a decapeptide used for the treatment of cancer. Therapeutics for the treatment of hypertension and congestive heart failure (e.g. Captopril and Enalapril) are also synthesized from amino acid derivatives. Specific examples of the use of pyridine and piperidine based amino acids are include thrombin inhibitors and GPIIb/IIIa antagonists (Adang, A. E. P., Peters, C. A. M., Gerritsma, S., Zwart, E., and Veeneman, G., Bioorganic & Medicinal Chemistry Letters 9: 1227–1232 (1999)). In addition, such compounds may be used to develop reagents for cleavage of DNA, and thus may be used as anti-cancer agents.

As reported in the literature, a number of routes are known for the synthesis of alpha-amino acids. The best known route to alpha-amino acids is the Strecker synthesis route (see, Introduction to Organic Chemistry, Streitwieser and Heathcock, Macmillan Publishing Co., Inc. New York, 1981). In this method a suitable aldehyde is treated with ammonia and HCN, so that an alpha-amino nitrile is formed, which is subsequently subjected to a hydrolysis reaction to provide the corresponding alpha-amino acid.

Also, it has been shown (see, Ugi, I. Angew. Chem., Intl. Ed. Engl., 1982, Vol. 21, pp. 810–819) that the reaction of an isocyanide ($X^1$—NC) with a carboxylic acid ($X^2$—$CO_2H$), an aldehyde ($X^3$—CHO) and an amine ($X^4$—$NH_2$) under the appropriate conditions provides the corresponding dipeptide (N-alkyl-N-acylalpha amino amide) as follows:

$$X^1-NC+X^2-CO_2H+X^3-CHO+X^4-NH_2 \rightarrow X^2-CO-NX^4-CHX^3-CO_2H$$

In an attempt to convert the dipeptides to their corresponding alpha-amino acids, chiral ferrocenylamine was used in the above-mentioned reaction. The desired amino acids were obtained with low to modest diastereoselectivity. (See, Sigmüller, et al., Tetrahedron, 1986, Vol. 42, pp. 5931–5940).

The use of a convertible isocyanide in the Ugi reaction, namely cyclohexene-isocyanide, followed by hydrolysis to provide the corresponding peptide carboxylic acid, has been demonstrated (see, Keating, T. A., et al., J. Am. Chem. Soc., 1996, Vol. 118, p. 2574) as follows:

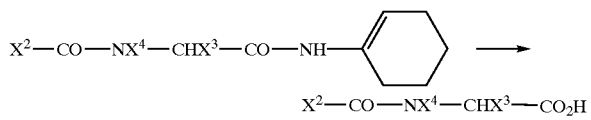
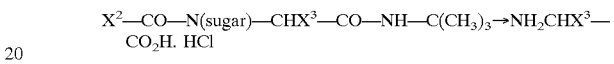

In addition, the use of phenyl-isocyanide and pyridyl-isocyanide was demonstrated in the conversion of dipeptides into pyrrole derivatives (see, Mjalli, et al., Tetrahedron. Lett., 1996, Vol. 37, pp. 2943–2946).

Moreover, the use of sugar derivatives (protected galactososylamine and arabinopyranosylamine) as chiral amines with t-butyl-isocyanide converted dipeptides into the corresponding sugar dipeptides, which were then converted in four chemical steps using very harsh conditions to produce the corresponding alpha-amino acids as shown below:

$$X^2-CO-N(sugar)-CHX^3-CO-NH-C(CH_3)_3 \rightarrow NH_2CHX^3-CO_2H \cdot HCl$$

where $X^3$=—Ph, —$^tBu$, —$(CH_2)_3$—COOH, —Bn, or -para-Cl—Ph (Kunz, H. et al., Tetrahedron. Lett., 1989, Vol. 30, pp. 4109–4110).

Also, it has been reported (see, Demharter, A. et al., Angew. Chem. Intl. Ed. Engl., 1996, Vol. 35, p. 173) that the reaction of unprotected alpha-amino acids (namely valine, phenyl alanine and proline) with a series of isocyanides and aldehydes in MeOH provided the corresponding three amino peptides with excellent yield and good diastereoselectivity as shown below:

$$X^4-NC+NH_2-CXH-CO_2H+X^3-CHO \rightarrow X^4-NH-CO-CHX^3-NH-CHX-CO_2Me$$

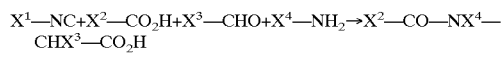

N-alkyl-N-acyl-alpha amino amide.

SUMMARY OF INVENTION

The present invention provides certain alpha-amino acetic acids and derivatives thereof, such as, but not limited to, esters, amides and salts. The present invention also provides a novel method for the synthesis of alpha-amino acids and derivatives thereof.

The invention provides alpha-amino acids and derivatives thereof as shown in Formula (1):

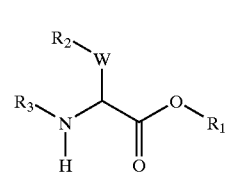

Formula (1)

wherein W comprises a $C_1$–$C_6$ alkylene group or a direct bond. $R_1$ comprises hydrogen or a $C_1$–$C_6$ alkylene group. $R_2$ comprises an alkyl, cycloalkyl, heterocyclyl, aryl, heteroaryl, fused cycloalkylaryl, fused arylcycloalkyl, fused heterocyclylaryl, fused arylheterocyclyl, fused cycloalkylheteroaryl, fused heteroarylcycloalkyl, fused heterocyclylheteroaryl, and fused heteroarylheterocyclyl group, optionally substituted 1 to 7 times. $R_3$ comprises hydrogen or an amino protecting group.

The present invention also provides a method for the synthesis of compounds useful as intermediates in the preparation of compounds of Formula (1) along with methods for the preparation of compounds of Formula (1).

The method for preparing compounds of Formula (1) disclosed herein comprises reacting an aldehyde of the formula R₂—W—CHO with ammonium formate and a C₁–C₆ alkyl isocyanide, wherein R₂ and W are defined as in Formula (1). This reaction provides a compound of Formula (2):

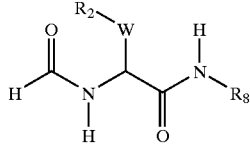

Formula (2)

which can be used to prepare compounds of Formula (1) using readily available starting materials and reagents, and conventional synthetic procedures.

DETAILED DESCRIPTION

The present invention provides certain alpha-amino acetic acids and derivatives thereof, such as, but not limited to, esters, amides and salts. The present invention also provides a novel method for the synthesis of alpha-amino acids and derivatives thereof The alpha-amino acids and derivatives thereof disclosed herein are useful in the discovery and development of new pharmaceuticals, agrochemical products, and nutraceuticals for the treatment of human disease, including cancer, AIDS, hypertension, atherosclerosis, diabetes, inflammation, and congestive heart failure.

The chemical methods used to prepare these derivatives of alpha-amino acids disclosed herein are amenable for production of these compounds in milligram to kilogram quantities from readily available materials. The method not only provides a wide range of currently known alpha-amino acids and derivatives thereof, but also provides new alpha-amino acids and derivatives thereof.

Further, the chemical method used to prepare these derivatives of alpha-amino acids disclosed herein does not use dangerous or highly poisonous materials such as hydrogen cyanide or sodium cyanide used in the Strecker synthesis. As a result, the method of the present invention to prepare alpha-amino acids and derivatives thereof is less hazardous to an individual than the Strecker method. Further, the waste generated from this method is less difficult to store, transport, and dispose of, as compared to the waste from the Strecker method, which contains unreacted hydrogen or sodium cyanide.

In the first aspect, the invention provides alpha-amino acids and derivatives thereof as shown in Formula (1):

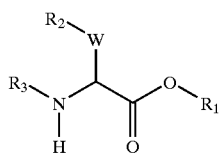

Formula (1)

wherein W comprises a C₁–C₆ alkylene group or a direct bond.

R₁ comprises hydrogen or a C₁–C₆ alkyl group.

R₂ comprises an alkyl, cycloalkyl, heterocyclyl, aryl, heteroaryl, fused cycloalkylaryl, fused arylcycloalkyl, fused heterocyclylaryl, fused arylheterocyclyl, fused cycloalkylheteroaryl, fused heteroarylcycloalkyl, fused heterocyclylheteroaryl, or fused heteroarylheterocyclyl group, optionally substituted 1 to 7 times with the following substituents a) -hydrogen;
b) -fluoro;
c) -chloro;
d) -bromo;
e) -iodo;
f) -cyano;
g) -nitro;
h) -perfluoroalkyl;
i) —T—R₄;
j) -alkyl;
k) -aryl;
l) -arylene-alkyl;
m) —T-alkyl;
n) —T-alkylene-aryl;
o) —T-alkylene-arylene-aryl;
p) —T-alkylene-arylene-alkyl; or
q) -arylene-T-alkyl;

wherein T comprises —CH₂—, —O—, —N(R₄)—; wherein R₄ and R₅ independently comprise: -hydrogen, -alkyl, or -aryl; and wherein two alkyl group substituents may be taken together to form a fused cycloalkyl ring. Preferably, R₂ comprises cycloalkyl, heterocyclyl, aryl, and heteroaryl groups. Preferred substituents comprise a fluoro, chloro, bromo, iodo, alkyl, or aryl group. More preferably, R₂ comprises a phenyl, naphthyl, thienyl, cyclopentyl, tetrahydropyranyl, tetrahydrothiopyranyl, pentamethylenesulfone, pyridyl, piperidinyl, or benzothiofuranyl group. In an especially preferred embodiment, R₂ comprises a group of the formula

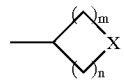

wherein n equals 1, 2, 3 or 4, and m equals 0, 1, or 2, wherein n plus m equals 3 or 4; and X comprises —O—, —NH—, —S—, or —SO₂—. In another especially preferred embodiment, R₂ comprises a 2-pyridyl, 3-pyridyl, or 4-pyridyl group. In another especially preferred embodiment, R₂ comprises a 2-thienyl, 3-thienyl, or 3-benzothiofuranyl group. In another especially preferred embodiment, R₂ comprises a 3,5-dichlorophenyl, 4-bromo phenyl, 4-biphenyl, or a 2-naphthalene group. In another especially preferred embodiment, R₂ comprises a group of the formula

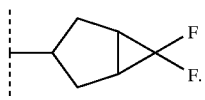

R₃ comprises hydrogen or an amino protecting group such as, but not limited to, the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("Fmoc"), t-butoxycarbonyl ("Boc"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl. Preferably, $R_3$ comprises hydrogen, 9-fluorenylmethoxycarbonyl ("Fmoc"), or t-butoxycarbonyl ("Boc").

The species of amino-protecting group employed is not critical so long as the derivatized amino group is stable to the condition of subsequent reaction(s) on other positions of the compound of Formula (1) and can be removed without disrupting the remainder of the molecule. Preferred amino-protecting groups are the t-butoxycarbonyl (Boc), 9-fluorenylmethoxycarbonyl (Fmoc), benzyloxycarbonyl (CBZ), allyloxycarbonyl, and the trityl groups. Further examples of groups referred to by the above terms T. W. Greene, "Protective Groups in Organic Synthesis", John Wiley and Sons, New York, N.Y., 1981, Chapter 7. The related term "protected amino" defines an amino group substituted with an amino-protecting group discussed above. The above protecting groups can be attached and removed utilizing methodology known per se in the art.

The alkyl, cycloalkyl, heterocyclyl, aryl, heteroaryl, fused cycloalkylaryl, fused arylcycloalkyl, fused heterocyclylaryl, fused arylheterocyclyl, fused cycloalkylheteroaryl, fused heteroarylcycloalkyl, fused heterocyclylheteroaryl, fused heteroarylheterocyclyl, alkylene, and arylene groups in $R_1$, $R_2$, $R_3$, $R_4$, $R_5$, and W may be optionally substituted 1 to 4 times with a substituent group, wherein said substituent group(s) or the term substituted refers to groups comprising:

a) -hydrogen;
b) -fluoro;
c) -chloro;
d) -bromo;
e) -iodo;
f) -cyano;
g) -nitro;
h) -perfluoroalkyl;
i) —Q—$R_6$;
j) -alkyl; or
k) -aryl;

wherein Q comprises: —$CH_2$—, —O—, —N($R_7$)—, wherein $R_6$ and $R_7$ independently comprise: -hydrogen, -alkyl, -aryl, or -alkylene-aryl.

Also included within the scope of the invention are the individual enantiomers of the compounds represented by Formula (1) above as well as any wholly or partially racemic mixtures thereof. The present invention also covers the individual enantiomers of the compounds represented by Formula (1) above as mixtures with diastereoisomers thereof in which one or more stereo-centers are inverted.

As used herein the term strong acid in aqueous media refers to HCl, $H_2SO_4$, $HNO_3$, $HClO_4$, $H_3PO_4$, and the like.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or $S(O)_2$ atoms. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or $S(O)_2$ atoms. Examples of "alkylene" as used herein include, but are not limited to, methylene, ethylene, and the like.

As used herein, the term "alkenyl" refers to a hydrocarbon radical having from two to ten carbons and at least one carbon—carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or $S(O)_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may containing one or more O, S, S(O), or $S(O)_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or S(O)$_2$ atoms.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may containing one or more O, S, S(O), or S(O)$_2$ atoms. Examples of "alkynylene" as used herein include, but are not limited to, ethyne-1,2-diyl, propyne-1,3-diyl, and the like.

As used herein, "cycloalkyl" refers to a alicyclic hydrocarbon group optionally having one or more degrees of unsaturation, having from three to twelve carton atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally having one or more degrees of unsaturation containing one or more heteroatomic substitutions selected from S, SO, S$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidne-2,4-diyl, piperidine-1,4-diyl, pyrrolidine-1,3-diyl, morpholine-2,4-diyl, piperazine-1,4-dyil, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

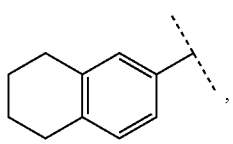

and the like.

As used herein, the term "fused cycloalkylarylene" refers to a fused cycloalkylaryl, wherein the aryl group is divalent. Examples include

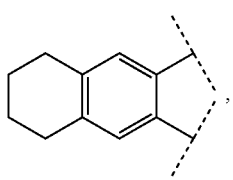

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

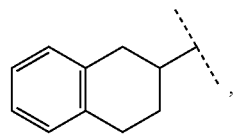

and the like.

As used herein, the term "fused arylcycloalkylene" refers to a fused arylcycloalkyl, wherein the cycloalkyl group is divalent. Examples include

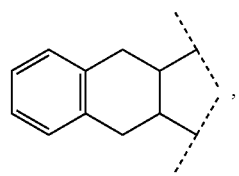

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

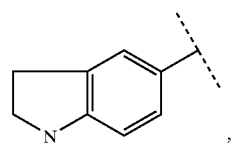

and the like

As used herein, the term "fused heterocyclylarylene" refers to a fused heterocyclylaryl, wherein the aryl group is divalent. Examples include

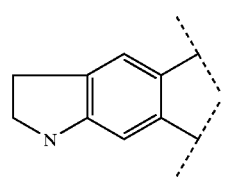

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

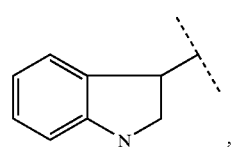

and the like.

As used herein, the term "fused arylheterocyclylene" refers to a fused arylheterocyclyl, wherein the heterocyclyl group is divalent. Examples include

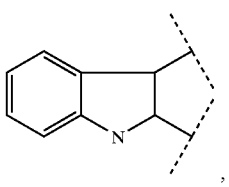

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

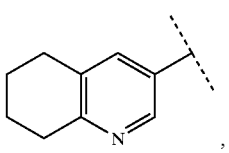

and the like.

As used herein, the term "fused cycloalkylheteroarylene" refers to a fused cycloalkylheteroaryl, wherein the heteroaryl group is divalent. Examples include

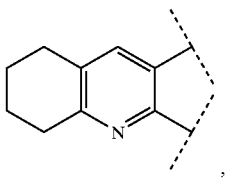

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include 5-aza-1-indanyl,

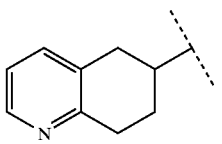

and the like.

As used herein, the term "fused heteroarylcycloalkylene" refers to a fused heteroarylcycloalkyl, wherein the cycloalkyl group is divalent. Examples include

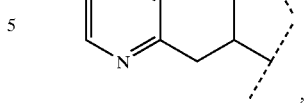

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl,

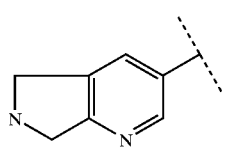

and the like.

As used herein, the term "fused heterocyclylheteroarylene" refers to a fused heterocyclylheteroaryl, wherein the heteroaryl group is divalent. Examples include

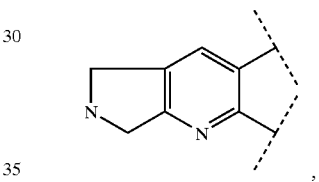

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include -5-aza-2,3-dihydrobenzofuran-2-yl,

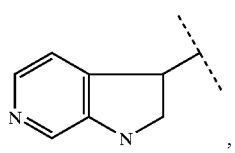

and the like.

As used herein, the term "fused heteroarylheterocyclylene" refers to a fused heteroarylheterocyclyl, wherein the heterocyclyl group is divalent. Examples include

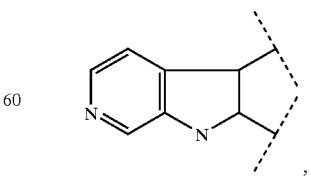

and the like.

As used herein, the term "direct bond", where part of a structural variable specification, refers to the direct joining of the substituents flanking (preceding and succeeding) the variable taken as a "direct bond".

As used herein, the term "alkoxy" refers to the group $R_aO-$, where $R_a$ is alkyl.

As used herein, the term "alkenyloxy" refers to the group $R_aO-$, where $R_a$ is alkenyl.

As used herein, the term "alkynyloxy" refers to the group $R_aO-$, where $R_a$ is alkynyl.

As used herein, the term "alkylsulfanyl" refers to the group $R_aS-$, where $R_a$ is alkyl.

As used herein, the term "alkenylsulfanyl" refers to the group $R_aS-$, where $R_a$ is alkenyl.

As used herein, the term "alkynylsulfanyl" refers to the group $R_aS-$, where $R_a$ is alkynyl.

As used herein, the term "alkylsulfenyl" refers to the group $R_aS(O)-$, where $R_a$ is alkyl.

As used herein, the term "alkenylsulfenyl" refers to the group $R_aS(O)-$, where $R_a$ is alkenyl.

As used herein, the term "alkynylsulfenyl" refers to the group $R_aS(O)-$, where $R_a$ is alkynyl.

As used herein, the term "alkylsulfonyl" refers to the group $R_aSO_2-$, where $R_a$ is alkyl.

As used herein, the term "alkenylsulfonyl" refers to the group $R_aSO_2-$, where $R_a$ is alkenyl.

As used herein, the term "alkynylsulfonyl" refers to the group $R_aSO_2-$, where $R_a$ is alkynyl.

As used herein, the term "acyl" refers to the group $R_aC(O)-$, where $R_a$ is alkyl, alkenyl, alkynyl, cycloalkyl, cycloalkenyl, or heterocyclyl.

As used herein, the term "aroyl" refers to the group $R_aC(O)-$, where $R_a$ is aryl.

As used herein, the term "heteroaroyl" refers to the group $R_aC(O)-$, where $R_a$ is heteroaryl.

As used herein, the term "alkoxycarbonyl" refers to the group $R_aOC(O)-$, where $R_a$ is alkyl.

As used herein, the term "acyloxy" refers to the group $R_aC(O)O-$, where $R_a$ is alkyl, alkenyl, alkynyl, cycloalkyl, cycloalkenyl, or heterocyclyl.

As used herein, the term "aroyloxy" refers to the group $R_aC(O)O-$, where $R_a$ is aryl.

As used herein, the term "heteroaroyloxy" refers to the group $R_aC(O)O-$, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example $-CH_2-O-CH_2-$, $-CH_2-SO_2-CH_2-$, $-CH_2-NH-CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl or cycloalkyl substituents shall be recognized as being functionally equivalent to those having one or more degrees of unsaturation. Designated numbers of carbon atoms (e.g. $C_1$–$C_{10}$ or $C_1$–$C_6$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent $=O$.

As used herein, the term "halogen" or "halo" shall include iodine, bromine, chlorine and fluorine.

As used herein, the term "mercapto" shall refer to the substituent $-SH$.

As used herein, the term "carboxy" shall refer to the substituent $-COOH$.

As used herein, the term "cyano" shall refer to the substituent $-CN$.

As used herein, the term "aminosulfonyl" shall refer to the substituent $-SO_2NH_2$.

As used herein, the term "carbamoyl" shall refer to the substituent $-C(O)NH_2$.

As used herein, the term "sulfanyl" shall refer to the substituent $-S-$.

As used herein, the term "sulfenyl" shall refer to the substituent $-S(O)-$.

As used herein, the term "sulfonyl" shall refer to the substituent $-S(O)_2-$.

Abbreviations used in the Examples are as follows:

| | |
|---|---|
| g = | grams |
| mg = | milligrams |
| L = | liters |
| mL = | milliliters |
| psi = | pounds per square inch |
| M = | molar |
| N = | normal |
| mM = | millimolar |
| mol = | moles |
| mmol = | millimoles |
| mbar = | millibar |
| rt = | room temperature |
| min = | minutes |
| h = | hours |
| mp = | melting point |
| MeOH = | methanol |
| EtOAc = | ethyl acetate |
| HCl = | hydrochloric acid |
| Conc. HCl = | concentrated hydrochloric acid |
| $HCO_2NH_4$ = | ammonium formate |
| t-BuNC = | t-butyl isocyanide |
| $Pd(OH)_2/C$ = | palladium hydroxide |
| Ether = | diethyl ether |
| $Na_2SO_4$ = | sodium sulfate |
| $H_2$ = | hydrogen gas |
| hr = | hours |
| d = | days |
| min = | minutes |

The present invention provides a method for the synthesis of compounds useful as intermediates in the preparation of compounds of Formula (1) along with methods for the preparation of compounds of Formula (1) using readily available starting materials, reagents and conventional synthesis procedures. In these reactions, it is also possible to make use of variants which are themselves known to those of ordinary skill in this art, but are not mentioned in greater detail.

In a second aspect, the present invention provides a method for preparing compounds of Formula (1) comprising reacting an aldehyde of formula $R_2-W-CHO$ with ammonium formate and a $C_1$–$C_6$ alkyl isocyanide, wherein $R_2$ and W are defined as in Formula (1). (See Scheme 1). This reaction provides a compound of Formula (2):

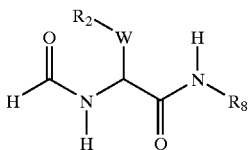

Formula (2)

wherein W comprises a $C_1$–$C_6$ alkylene group or a direct bond, and $R_8$ comprises a $C_1$–$C_6$ alkyl group.

$R_2$ comprises an alkyl, cycloalkyl, heterocyclyl, aryl, heteroaryl, fused cycloalkylaryl, fused arylcycloalkyl, fused heterocyclylaryl, fused arylheterocyclyl, fused cycloalkylheteroaryl, fused heteroarylcycloalkyl, fused heterocyclylheteroaryl, or fused heteroarylheterocyclyl group, optionally substituted 1 to 7 times with the following substituents a) -hydrogen;
b) -fluoro;
c) -chloro;
d) -bromo;
e) -iodo;
f) -cyano;
g) -nitro;
h) -perfluoroalkyl;
i) —T—$R_4$;
j) -alkyl;
k) -aryl;
l) -arylene-alkyl;
m) —T-alkyl;
n) —T-alkylene-aryl;
o) —T-alkylene-arylene-aryl;
p) —T-alkylene-arylene-alkyl; or
q) -arylene-T-alkyl;

wherein T comprises —$CH_2$—, —O—, —N($R_4$)—; wherein $R_4$ and $R_5$ independently comprise: -hydrogen, -alkyl, or -aryl; and wherein two alkyl group substituents may be taken together to form a fused cycloalkyl ring. Preferably, $R_2$ comprises cycloalkyl, heterocyclyl, aryl, and heteroaryl groups. Preferred substituents comprise fluoro, chloro, bromo, iodo, alkyl, and aryl groups. More preferably, $R_2$ comprises a phenyl, naphthyl, thienyl, cyclopentyl, tetrahydropyranyl, tetrahydrothiopyranyl, pentamethylenesulfone, pyridyl, piperidinyl, or benzothiofuranyl group. In an especially preferred embodiment, $R_2$ comprises a group of the formula

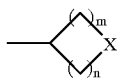

wherein n equals 1, 2, 3 or 4, and m equals 0, 1, or 2, wherein n plus m equals 3 or 4; and X comprises —O—, —NH—, —S—, or —$SO_2$—. In another especially preferred embodiment, $R_2$ comprises a 2-pyridyl, 3-pyridyl, or 4-pyridyl group. In another especially preferred embodiment, $R_2$ comprises a 2-thienyl, 3-thienyl, or 3-benzothiofuranyl group. In another especially preferred embodiment, $R_2$ comprises a 3,5-dichlorophenyl, 4-bromo phenyl, 4-biphenyl, or a 2-naphthalene group. In another especially preferred embodiment, $R_2$ comprises a group of the formula

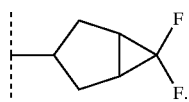

The cycloalkyl, heterocyclyl, aryl, heteroaryl, fused cycloalkylaryl, fused arylcycloalkyl, fused heterocyclylaryl, fused arylheterocyclyl, fused cycloalkylheteroaryl, fused heteroarylcycloalkyl, fused heterocyclylheteroaryl, fused heteroarylheterocyclyl, alkylene, and arylene groups in $R_1$, $R_2$, $R_3$, $R_4$, $R_5$, and W may be optionally substituted 1 to 4 times with a substituent group, wherein said substituent group(s) or the term substituted refers to groups comprising:

a) -hydrogen;
b) -fluoro;
c) -chloro;
d) -bromo;
e) -iodo;
f) -cyano;
g) -nitro;
h) -perfluoroalkyl;
i) —Q—$R_6$;
j) -alkyl; or
k) -aryl;

wherein Q comprises: —$CH_2$—, —O—, —N($R_7$)—, wherein $R_6$ and $R_7$ independently comprise: -hydrogen, -alkyl, -aryl, or -alkylene-aryl.

Compounds of Formula (2) can be converted into compounds of Formula (1a) using strong acid, such as concentrated HCl, to hydrolyze the formamide and amide as shown in Scheme 1.

Scheme 1

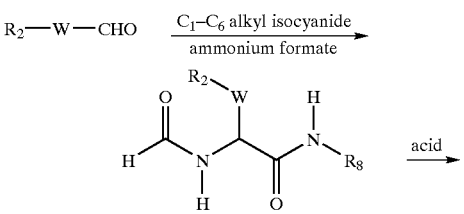

Formula (2)

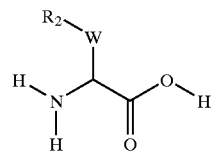

Formula (1a)

A general procedure for converting compounds of Formula (2) to the corresponding amino acid or acid salt thereof is described in General Procedure B.

Compounds of Formula (1a) can be converted into numerous other compounds of Formula (1) as shown in Schemes 2 through 5.

In one aspect compounds of Formula (1a) can be converted to esters of Formula (1b), wherein $R_1$ comprises a $C_1$–$C_6$ alkyl group. (See Scheme 2).

Scheme 2

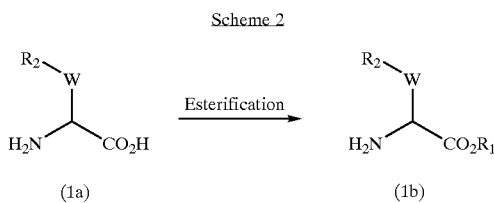

Standard esterification conditions can be used to convert compounds of Formula (1a) to the corresponding ester. For example, the carboxyl group of Formula (1a) can be activated with $SOCl_2$ in the presence of a $C_1$–$C_6$ alkyl alcohol to produce compounds of Formula (1b). A procedure for converting compounds of Formula (1a) to the corresponding ester of Formula (1b) is described in General Procedure H.

In another aspect, compounds Formula (1a) comprising at least one unit of unsaturation in $R_2$ may be reduced to produce a compound of Formula (1c) wherein $R_2'$ comprises a fully saturated group. (See Scheme 3).

Scheme 3

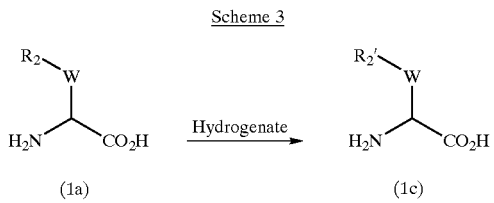

A preferred method of reduction comprises uses a metal catalyst and hydrogen under pressure. Metal catalysts useful for reducing the $R_2$ side chain include, but are not limited to, palladium on carbon (Pd/C), palladium hydroxide (Pd(OH)$_2$/C), and Rh(PPh$_3$)$_3$. For example, a compound of Formula (1a) wherein $R_2$ comprises a 4-pyridyl group can be converted to a compound of Formula (1c) wherein $R_2'$ comprises a 4-piperidinyl group using a metal catalyst comprising palladium hydroxide and hydrogen under pressure. A procedure for converting compounds of Formula (1a) wherein $R_2'$ comprises a 4-pyridyl group to a compound of Formula (1c) wherein $R_2$ comprises a 4-piperidinyl group is described in General Procedure E.

The amino group of compounds of Formula (1a) can be protected with a protecting group to form compounds of Formula (1d). (See Scheme 4).

Scheme 4

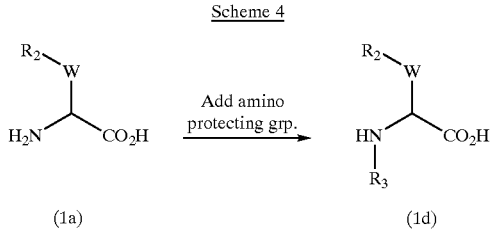

For the compound of Formula (1d), $R_3$ comprises an amino protecting group such as, but not limited to, the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycrbonyl, 4-chlorobenzyloxycarbonyl, 3-chlorobenzyloxycarbonyl, 2-chlorobenzyloxycarbonyl, 2,4-dichlorobenzyloxycarbonyl, 4,-bromobenzyloxycarbonyl, 3-bromobenzyloxycarbonyl, 4-nitrobenzyloxycarbonyl, 4-cyanobenzyloxy-carbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclo pentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino) ethoxycarbonyl, 9-fluorenylmethoxycarbonyl ("Fmoc"), t-butoxycarbonyl ("Boc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxy carbonyl, 2-ethynyl-2-propoxycarbonyl, cyclopropylmethoxycarbonyl, 4-(decyloxy) benzyloxycarbonyl, isobomyloxycarbonyl, 1-piperidyloxycarbonyl. Preferably, $R_3$ comprises 9-fluorenylmethoxycarbonyl ("Fmoc"), or t-butoxycarbonyl ("Boc").

A method for attaching the Fmoc group to compounds of Formula (1a) comprises the addition of the trimethylsilyl chloride to a mixture of a compound of Formula (1a) and a hindered amine base, and then adding 9-fluorenylmethoxyacid chloride ("Fmoc-Cl"). A procedure for converting compounds of Formula (1a) to a compound of Formula (1d) wherein $R_3$ comprises an Fmoc group is described in General Procedure C.

A method for attaching the Boc group to compounds of Formula (1a) comprises the addition of Boc anhydride ((Boc)$_2$O) to a mixture of a compound of Formula (1a) and a base. A general procedure for converting compounds of Formula (1a) to a compound of Formula (1d) wherein $R_3$ comprises a Boc group is described in General Procedure F.

In a further aspect, the present invention provides a method to synthesize compounds of Formula (1e). (See Scheme 5)

Scheme 5

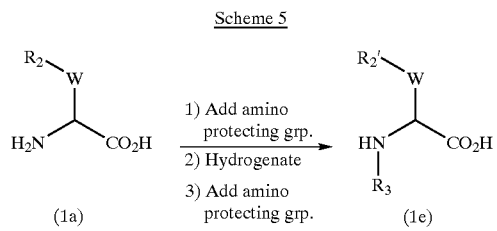

For the compound of Formula (1e), $R_2'$ comprises a heterocyclyl group wherein the heteroatom or atoms comprise nitrogen. Preferably, $R_2'$ comprises a group of the formula

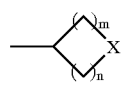

wherein n equals 1, 2, 3 or 4, and m equals 0, 1, or 2, wherein n plus m equals 3 or 4; and X comprises —N($R_{10}$)—, wherein $R_{10}$ comprises hydrogen or an amino protecting group such as but not limited to the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl-2-methylcyclohexanyloxycarbonyl, 2-(4-toluylsulfonyl)ethoxycarbonyl, 2(methylsulfonyl)ethoxycarbonyl, 2-(triphenylphosphino) ethoxycarbonyl, 9-fluorenylmethoxycarbonyl ("Fmoc"), t-butoxycarbonyl ("Boc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxy carbonyl, 2-ethynyl-2-propoxycarbonyl, cyclopropylmethoxycarbonyl, 4-(decyloxy) benzyloxycarbonyl, isobomyloxycarbonyl, 1-piperidyloxycarbonyl. Preferably, $R_{10}$ comprises 9-fluorenylmethoxycarbonyl ("Fmoc"), or t-butoxycarbonyl ("Boc").

The method to synthesize compounds of Formula (1e) uses compounds of Formula (1a) wherein $R_2$ comprises heteroaryl, fused heterocyclylaryl, fused arylheterocyclyl, fused cycloalkylheteroaryl, fused heteroarylcycloalkyl, fused heterocyclylheteroaryl, or fused heteroarylheterocyclyl wherein the heteroatom or atoms comprises nitrogen. Preferred embodiments of the method to synthesize compounds of Formula (1e) use compounds of Formula (1a) wherein $R_2$ comprises a 2-pyridyl, 3-pyridyl, or 4-pyridyl group.

In one preferred embodiment of the method to synthesize compounds of Formula (1e), the compound of Formula (1a), wherein $R_2$ comprises 3-pyridyl, is added to a mixture of trimethylsilyl chloride and a hindered amine base, and then 9-fluorenyl methoxyacid chloride (Fmoc-Cl) is added. After attaching the Fmoc group to the alpha amino group, the Fmoc intermediate is added to a mixture of palladium hydroxide and (Boc)$_2$O and placed under hydrogen pressure. The resulting compound of Formula (1e), wherein $R_3$ comprises an Fmoc group, $R_2'$ comprises

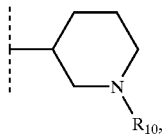

wherein $R_{10}$ comprises a Boc group, is then isolated. A procedure for converting compounds of Formula (1a) to compounds of Formula (1e) wherein $R_3$ comprises an Fmoc group, and $R_2'$ comprises

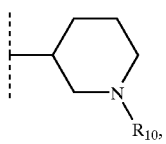

wherein $R_{10}$ comprises a Boc group, is described in General Procedures C and D.

In another preferred embodiment of the method to synthesize compounds of Formula (1e), the compound of Formula (1a), wherein $R_2$ comprises 4-pyridyl, is added to a mixture of (Boc)$_2$O and a base. After attachment of the Boc group to the alpha amino group, the Boc intermediate is added to a mixture of palladium hydroxide and hydrogen under pressure. The resulting compound of Formula (1e), wherein $R_2'$ comprises

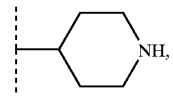

and $R_3$ comprises a Boc group, is then isolated. A general procedure for converting compounds of Formula (1a) to a compound of Formula (1e), wherein $R_2'$ comprises

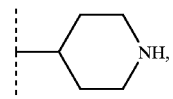

and $R_3$ comprises a Boc group is described in General Procedures F and G.

The following general procedures can be used to synthesize compounds of Formula (1) and derivatives thereof.

Procedure A

To an aldehyde (1 mole) in methanol (1 L) was added ammonium formate (3 moles) and t-butyl isocyanide (1.5 moles) and the mixture was heated at 65° C. for 12 h. The reaction mixture was cooled to room temperature and the methanol was removed under reduced pressure. The resulting solid material was dissolved in ethyl acetate and washed with water. The organic layer was dried using excess Na$_2$SO$_4$ and concentrated under reduced pressure to give the Ugi adduct (60%–99% yield).

Procedure B

The Ugi adduct obtained in step A was dissolved in concentrated HCl (1 L) and the mixture was heated at 100° C. for 24 h. The water was removed under reduced pressure and the resulting solid was recrystallized from MeOH/Ether to give the amino acid (40%–84% yield).

Procedure C

To the amino acid (0.44 mole, obtained in step B) and N,N-diisopropylethylamine (1.76 mole) in CH$_2$Cl$_2$ (2 L) at −10° C., trimethylsilyl chloride (0.88 mole) was added. The reaction mixture was stirred for 10 min. at the same temperature and then Fmoc-Cl was added. The reaction temperature was slowly brought to 30° C. and stirred for additional 12 h. The solvent was evaporated and the residue was dissolved in 10% aq. Na$_2$CO$_3$ solution. The aqueous layer was washed with ether and cooled to obtain the Fmoc-protected amino acid (64%–95% yield).

Procedure D

To the Fmoc amino acid (10 mmole, obtained in step C) in 1,4-dioxane (100 mL), Pd(OH)$_2$ (1 g) and (Boc)$_2$O was added. The mixture was stirred under H$_2$ pressure (60 psi) for 24 h. The catalyst was filtered and the filtrate was evaporated to get the N-Boc-protected piperidine derivative (60%–95% yield).

Procedure E

To the amino acid (10 mmoles, obtained in step B) in 2N HCl (100 mL), 10% Pd/C was added and the mixture was stirred under H$_2$ pressure (50 psi) for 18 h. The catalyst was filtered and the filtrate was evaporated to obtain the piperidine amino acid (70%–90% yield).

Procedure F

To the amino acid (10 mmole, obtained in step B) in a solvent mixture of 1,4-dioxane (100 mL) and water (100 mL) was added NaHCO$_3$ (40 mmole) and (Boc)$_2$O (12 mmole) and the resulting mixture was stirred at room temperature overnight. The dioxane was removed at reduced pressure and the aqueous solution was extracted with ether (2×100 mL). The pH of the aqueous solution was adjusted to pH 3 with 3 N HCl at 0° C. and the product was extracted with EtOAc (3×100 mL). The combined organic extracts were dried over anhydrous Na$_2$SO$_4$ and concentrated to dryness to yield the desired Boc-protected amino acid (75%–95% yield).

Procedure G

To the N-Boc amino acid (10 mmoles, obtained in step F) in 1,4-dioxane (50 mL), Pd(OH)$_2$ (0.25 g) was added and the mixture was stirred under H$_2$ pressure (60 psi) for 3 days. The catalyst was filtered and the filtrate was evaporated to obtain the piperidine N-Boc amino acid (60%–95% yield).

Procedure H

To the amino acid (0.32 mole, obtained in step B) in anhydrous methanol (800 mL) was added SOCl$_2$ (0.63 mol). The reaction mixture was heated to reflux for one hour and the solvent was evaporated to furnish the product (90–99% yield).

EXAMPLES

Example 1

Using an aldehyde of Formula (110) as starting material, a compound of Formula (111) was synthesized using General Procedures A, B, and C.

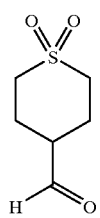

Formula (110)

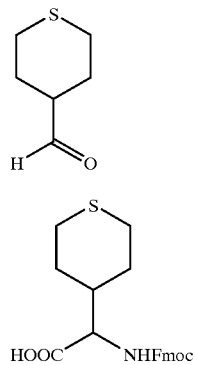

Formula (111)

The physical data for the compound of Formula (111) is as follows:

$^1$H NMR (300 MHz, CD$_3$OD): δ 7.77 (d, J=7.8, 2H), 7.59 (d, J=7.8, 2H), 7.43–7.29 (m, 4H), 5.31 (d, J=9.0, 1H), 4.46–4.18 (m, 4H), 2.75–2.45 (m, 4H), 2.08–1.50 (m, 5H).

Example 2

Using an aldehyde of Formula (120) as starting material, a compound of Formula (121) was synthesized using General Procedures A, B, and C.

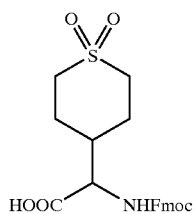

Formula (120)

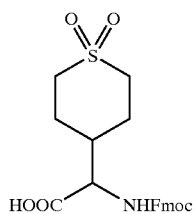

Formula (121)

The physical data for the compound of Formula (121) is as follows:

$^1$H NMR (300 MHz, DMSO-d$_6$): δ 7.90 (d, J=7.5, 2H), 7.82 (d, J=8.7, 1H), 7.75 (d, J=7.5, 2H), 7.45–7.31 (m, 3H), 4.35–4.21 (m, 3H), 4.10 (dd, J=8.7, 5.1, 1H), 3.28–2.98 (m, 4H), 2.22–1.63 (m, 5H).

Example 3

Using an aldehyde of Formula (130) as starting material, a compound of Formula (131) was synthesized using General Procedures A and B.

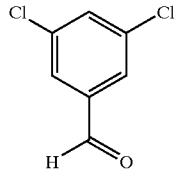

Formula (130)

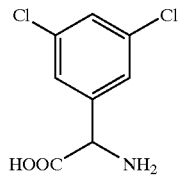

Formula (131)

The physical data for the compound of Formula (131) is as follows:

$^1$H NMR (300 MHz, D$_2$O): δ 7.66 (t, J=1.8, 1H), 7.55 (d, J=1.8, 2H), 5.04 (s, 1H).

Example 4

Using an aldehyde of Formula (130) as starting material, a compound of Formula (141) was synthesized using General Procedures A, B, and F.

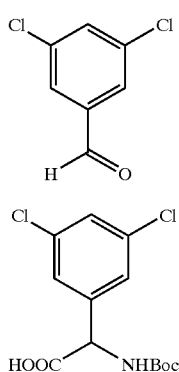

Formula (130)

Formula (141)

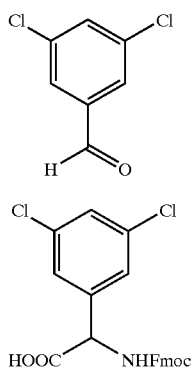

The physical data for the compound of Formula (141) is as follows:

$^1$H NMR (300 MHz, CDCl$_3$): δ 8.22 (d, J=4.5, 1H), 7.33–7.30 (m, 3H), 5.06 (d, J=4.5, 1H), 1.24 (s, 9H).

Example 5

Using an aldehyde of Formula (130) as starting material, a compound of Formula (151) was synthesized using General Procedures A, B, and C.

Formula (130)

Formula (151)

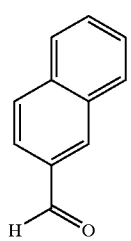

The physical data for the compound of Formula (151) is as follows:

$^1$H NMR (300 MHz, DMSO-d$_6$): δ 13.26 (brs, 1H), 8.33 (d, J=8.4, 1H), 7.90 (d, J=7.5, 2H), 7.74 (d, J=7.5, 2H), 7.60–7.29 (m, 7H), 5.29 (d, J=8.4, 1H), 4.37–4.21 (m, 3H).

Example 6

Using an aldehyde of Formula (160) as starting material, a compound of Formula (161) was synthesized using General Procedures A and B.

Formula (160)

Formula (161)

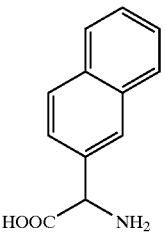

The physical data for the compound of Formula (161) is as follows:

$^1$H NMR (300 MHz, CD$_3$OD): δ 8.06–7.90 (m, 4H), 7.62–7.58 (m, 3H), 5.28 (s, 1H).

Example 7

Using an aldehyde of Formula (160) as starting material, a compound of Formula (171) was synthesized using General Procedures A, B, and F.

Formula (160)

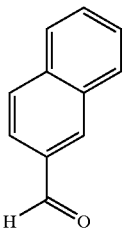

Formula (171)

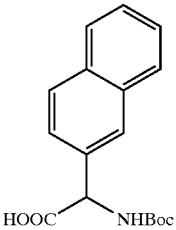

The physical data for the compound of Formula (171) is as follows:

$^1$H NMR (300 MHz, CD$_3$OD): δ 7.88–7.84 (m, 4H), 7.54–7.47 (m, 3H), 5.36 (s, 1H), 1.45 (s, 9H).

Example 8

Using an aldehyde of Formula (160) as starting material, a compound of Formula (181) was synthesized using General Procedures A, B, and C.

Formula (160)

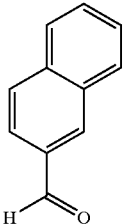

-continued

Formula (181)

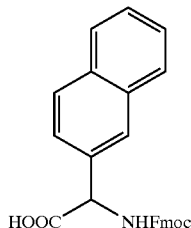

The physical data for the compound of Formula (181) is as follows:

$^1$H NMR (300 MHz, DMSO-d$_6$): δ 13.02 (brs, 1H), 8.38 (d, J=8.4, 1H), 8.00–7.22 (m, 15H), 5.38 (d, J=8.4, 1H), 4.32–4.21 (m, 3H).

Mass Spec: m/z: 425 (M+2H)$^+$.

Example 9

Using an aldehyde of Formula (190) as starting material, a compound of Formula (191) was synthesized using General Procedures A and B.

Formula (190)

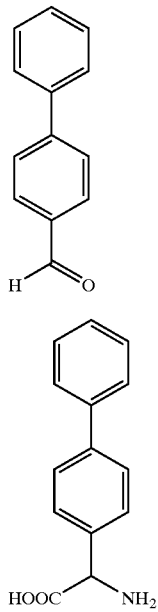

(Formula (191))

The physical data for the compound of Formula (191) is as follows:

$^1$H NMR (300 MHz, DMSO-d$_6$): δ 9.05 (brs, 2H), 7.78–7.38 (m, 9H), 5.15 (s, 1H).

Mass Spec: m/z: 228 (M+H)$^+$.

Example 10

Using an aldehyde of Formula (190) as starting material, a compound of Formula (211) was synthesized using General Procedures A, B, and F.

Formula (190)

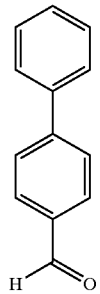

Formula (201)

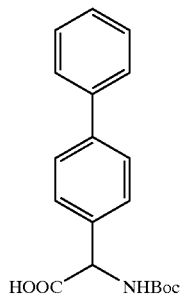

The physical data for the compound of Formula (201) is as follows:

$^1$H NMR (300 MHz, CD$_3$OD): δ 7.62–7.30 (m, 9H), 5.23 (s, 1H), 1.45 (s, 9H).

Example 11

Using an aldehyde of Formula (190) as starting material, a compound of Formula (211) was synthesized using General Procedures A, B, and C.

Formula (190)

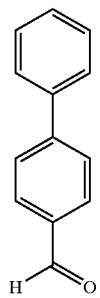

Formula (211)

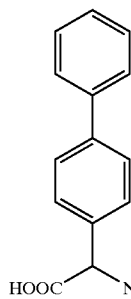

The physical data for the compound of Formula (211) is as follows:

$^1$H NMR (300 MHz, DMSO-d$_6$): δ 8.27 (d, J=8.4, 1H), 7.91–7.29 (m, 17H), 5.22 (d, J=8.4, 1H), 4.31–4.21 (m, 3H).

Mass Spec: m/z: 450 (M+H)$^+$.

Example 12

Using an aldehyde of Formula (220) as starting material, a compound of Formula (221) was synthesized using General Procedures A and B.

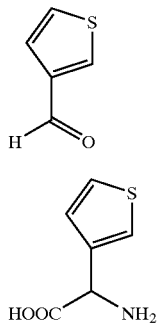

Formula (220)

Formula (221)

The physical data for the compound of Formula (221) is as follows:

$^1$H NMR (300 MHz, CD$_3$OD): δ 7.65–7.63 (m, 1H), 7.58–7.55 (m, 1H), 7.21 (dd, J=5.1 1.5, 1H), 5.23 (s, 1H).

Mass Spec: m/z: 158 (M+H)$^+$.

Example 13

Using an aldehyde of Formula (220) as starting material, a compound of Formula (231) was synthesized using General Procedures A, B, and F.

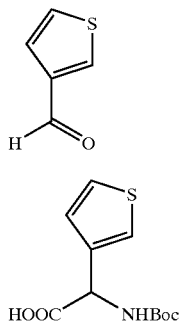

Formula (220)

Formula (231)

The physical data for the compound of Formula (231) is as follows:

$^1$H NMR (300 MHz, DMSO-d$_6$): δ 12.78 (brs, 1H), 7.61 (d, J=8.7, 1H), 7.50–7.48 (m, 2H), 7.15 (dd, J=4.8, 1.5, 1H), 5.19 (d, J=8.7, 1H), 1.39 (s, 9H).

Example 14

Using an aldehyde of Formula (220) as starting material, a compound of Formula (241) was synthesized using General Procedures A, B, and C.

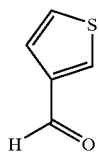

Formula (220)

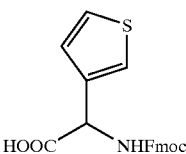

Formula (241)

The physical data for the compound of Formula (241) is as follows:

$^1$H NMR (300 MHz, DMSO-d$_6$): δ 12.90 (brs, 1H), 8.18 (d, J=8.4, 1H), 7.90 (d, J=7.5, 2H), 7.74 (d, J=7.5, 2H), 7.50–7.18 (m, 7H), 5.25 (d, J=8.4, 1H), 4.32–4.20 (m, 3H).

Mass Spec: m/z: 381 (M+2H)$^+$.

Example 15

Using an aldehyde of Formula (250) as starting material, a compound of Formula (251) was synthesized using General Procedures A and B.

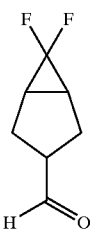

Formula (250)

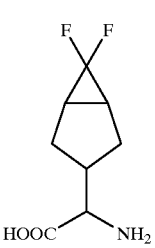

Formula (251)

The physical data for the compound of Formula (251) is as follows:

$^1$H NMR (300 MHz, D$_2$O): δ 3.87 (d, J=7.5, 1H), 2.52–2.36 (m, 1H), 2.24–1.90 (m, 6H).

Example 16

Using an aldehyde of Formula (250) as starting material, a compound of Formula (261) was synthesized using General Procedures A, B, and F.

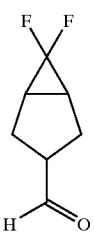

Formula (250)

-continued

Formula (261)

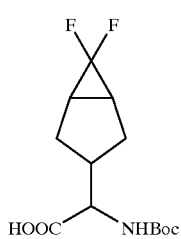

The physical data for the compound of Formula (261) is as follows:

$^1$H NMR (300 MHz, CDCl$_3$): δ 5.09 (d, J=8.7, 1H), 4.31–4.26 (m, 1H), 2.50–2.36 (m, 1H), 2.18–1.76 (m, 6H), 1.45 (s, 9H).

Example 17

Using an aldehyde of Formula (270) as starting material, a compound of Formula (271) was synthesized using General Procedures A, B, and C.

Formula (270)

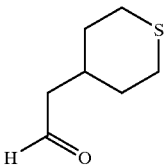

Formula (271)

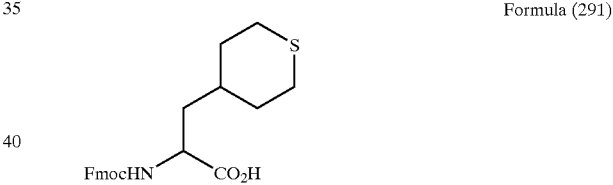

The physical data for the compound of Formula (271) is as follows:

$^1$H NMR (300 MHz, CDCl$_3$): δ 7.80–7.21 (m, 8H), 6.09 (d, 1H), 5.40 (d, J=8.5, 1H), 4.41 (m, 2H), 4.20 (m, 1H), 3.86 (m, 2H), 3.39 (m, 2H), 1.80–1.10 (m, 7H).

Mass Spec: m/z: 397 (M+2H)$^+$.

Example 18

Using an aldehyde of Formula (280) as starting material, a compound of Formula (281) was synthesized using General Procedures A, B, and F.

Formula (280)

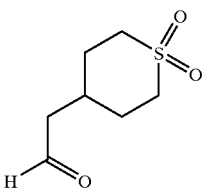

-continued

Formula (281)

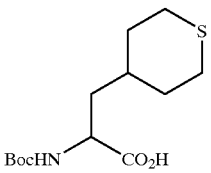

The physical data for the compound of Formula (281) is as follows:

$^1$H NMR (300 MHz, CDCl$_3$): δ 10.70 (brs, 1H), 6.40 and 4.98 (2 d, 1H), 4.40 and 4.20 (2 brs, 1H), 2.61 (m, 4H), 2.20–1.20 (m, 16H).

Mass Spec: m/z: 290 (M+1H)$^+$.

Example 19

Using an aldehyde of Formula (290) as starting material, a compound of Formula (291) was synthesized using General Procedures A, B, and C.

Formula (290)

Formula (291)

The physical data for the compound of Formula (291) is as follows:

$^1$H NMR (300 MHz, CDCl$_3$): δ 7.80–7.20 (m, 8H), 6.10 (brs, 1H), 5.21 (d, J=8.0, 1H), 4.50 (m, 3H), 2.60 (m, 4H), 2.00 (m, 3H), 1.40 (m, 4H).

Example 20

Using an aldehyde of Formula (300) as starting material, a compound of Formula (301) was synthesized using General Procedures A, B, and F.

Formula (300)

Formula (301)

[Structure: tetrahydrothiopyran-1,1-dioxide with CH2-CH(NHBoc)-CO2H substituent]

The physical data for the compound of Formula (301) is as follows:

$^1$H NMR (300 MHz, CDCl$_3$): δ 6.22 (brs, 1H), 4.21 (m, 1H), 3.00 (m, 4H), 2.25–1.60 (m, 7H), 1.40 (s, 9H).

Mass Spec: m/z: 644 [2×((M$^+$+1H)].

Example 21

Using an aldehyde of Formula (300) as starting material, a compound of Formula (311) was synthesized using General Procedures A, B, and C.

Formula (300)

[Structure: tetrahydrothiopyran-1,1-dioxide with CH2-CHO substituent]

Formula (311)

[Structure: tetrahydrothiopyran-1,1-dioxide with CH2-CH(NHFmoc)-CO2H substituent]

The physical data for the compound of Formula (311) is as follows:

$^1$H NMR (300 MHz, CDCl$_3$): δ 7.80–7.20 (m, 8H), 5.30 (d, J=8.3, 1H), 4.40 (m, 2H), 4.20 (m, 1H), 3.00 (m, 4H), 2.20–1.60 (m, 7H).

Example 22

Using an aldehyde of Formula (320) as starting material, a compound of Formula (321) was synthesized using General Procedures A and B.

Formula (320)

[Structure: 4-bromobenzaldehyde]

Formula (321)

[Structure: 4-bromophenyl-CH(NH2)-COOH]

The physical data for the compound of Formula (321) is as follows:

$^1$H NMR (300 MHz, D$_2$O): δ 7.50 (d, J=8.6, 2H), 7.20 (d, J=8.6, 2H), 4.87 (s, 1H).

Example 23

Using an aldehyde of the following Formula (320) as starting material, a compound of Formula (331) was synthesized using General Procedures A, B, and H.

Formula (320)

[Structure: 4-bromobenzaldehyde]

Formula (331)

[Structure: 4-bromophenyl-CH(NH2)-COOCH3]

The physical data for the compound of Formula (331) is as follows:

$^1$H NMR (300 MHz, CD$_3$OD): δ 7.50 (d, J=8.5, 2H), 7.20 (d, J=8.5, 2H), 4.39 (brs, 1H), 3.80 (s, 3H).

Example 24

Using an aldehyde of Formula (340) as starting material, a compound of Formula (341) was synthesized using General Procedures A and B.

Formula (340)

[Structure: pyridine-3-carboxaldehyde]

Formula (341)

[Structure: pyridin-3-yl-CH(NH2)-COOH]

The physical data for the compound of Formula (341) is as follows:

$^1$H NMR (300 MHz, D$_2$O): 8.85 (m, 1H), 8.75 (dd, 1H), 8.55 (dd, 1H), 8.05 (dd, 1H)

Example 25

Using an aldehyde of Formula (340) as starting material, a compound of Formula (351) was synthesized using General Procedures A, B, and F.

Formula (340)

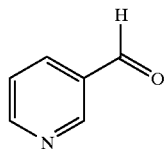

Formula (351)

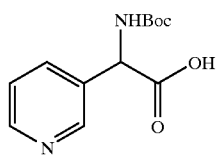

The physical data for the compound of Formula (351) is as follows:

$^1$H NMR (300 MHz, D$_2$O): δ 8.35 (s, 1H), 8.30 (d, 1H), 7.75 (dd, 1H), 7.30 (dd, 1H), 1.1 (s, 9H).

Mass Spec: m/z: 253 (M+1H)$^+$.

Example 26

Using an aldehyde of Formula (340) as starting material, a compound of Formula (361) was synthesized using General Procedures A, B, and C.

Formula (340)

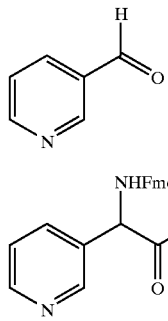

Formula (361)

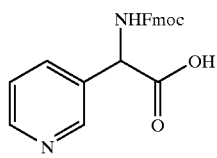

The physical data for the compound of Formula (361) is as follows:

$^1$H NMR (300 MHz, DMSO-d$_6$): δ 8.5 (bs, 1H), 8.35 (d, 1H), 7.85 (d, 2H), 7.65 (d, 3H), 7.4–7.2 (m, 6H), 4.7 (s, 1H), 4.2 (m, 3H).

Mass Spec: m/z: 376 (M+2H)$^+$.

Example 27

Using an aldehyde of Formula (340) as starting material, a compound of Formula (11) was synthesized using General Procedures A, B, C, and D.

Formula (340)

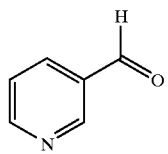

Formula (371)

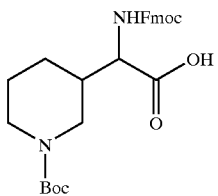

The physical data for the compound of Formula (371) is as follows:

$^1$H NMR (300 MHz, CDCl$_3$): δ 7.75 (d, 2H), 7.60 (m, 2H), 7.35 (m, 2H), 7.30 (m, 2H)), 5.7 (bs, 1H), 4.4 (m, 3H), 4.2 (t, 1H), 2.6 (m, 2H), 2.1–1.2 (m, 16H).

Example 28

Using an aldehyde of Formula (380) as starting material, a compound of Formula (381) was synthesized using General Procedures A and B.

Formula (380)

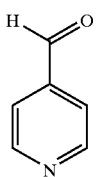

Formula (381)

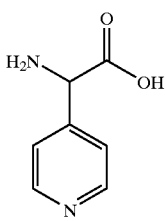

The physical data for the compound of Formula (381) is as follows:

$^1$H NMR (300 MHz, D$_2$O): δ 6 8.75 (d, 2H), 8.05 (d, 2H), 5.1 (s, 1H).

Mass Spec: m/z: 151 (M+−H).

Example 29

Using an aldehyde of Formula (380) as starting material, a compound of Formula (391) was synthesized using General Procedures A, B, F, and G.

Formula (380)

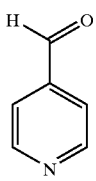

-continued

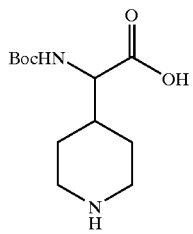

Formula (391)

The physical data for the compound of Formula (391) is as follows:

$^1$H NMR (300 MHz, CDCl$_3$): δ 4.65 (m, 1H), 3.1 (d, 2H), 2.95 (t, 2H), 2.3 m, 1H), 1.65 (d, 2H), 1.4 (s, 9H).

Mass Spec: m/z: 257 (M+−H).

Example 30

Using an aldehyde of Formula (380) as starting material, a compound of Formula (401) was synthesized using General Procedures A, B, and E.

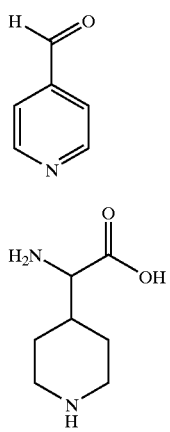

Formula (380)

Formula (401)

The physical data for the compound of Formula (401) is as follows:

1H NMR (300 MHz, D$_2$O): δ 3.22 (dd, 2H), 2.65 (m, 3H), 1.8 (m, 3H), 1.22 (m, 2H).

Mass Spec: m/z: 318[2× (M$^+$+2H)].

Example 31

Using an aldehyde of Formula (410) as starting material, a compound of Formula (411) was synthesized using General Procedures A and B.

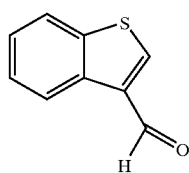

Formula (410)

-continued

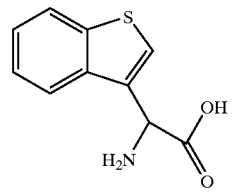

Formula (411)

The physical data for the compound of Formula (411) is as follows:

$^1$H NMR (300 MHz, D$_2$O): δ 8.1 (m, 3H), 7.5 (m, 2H), 5.6 (m, 1H).

Example 32

Using an aldehyde of Formula (420) as starting material, a compound of Formula (421) was synthesized using General Procedures A, B, and F.

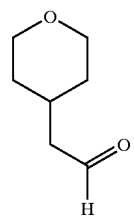

Formula (420)

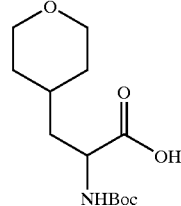

Formula (421)

The physical data for the compound of Formula (421) is as follows:

$^1$H NMR (300 MHz, CDCl$_3$): δ 5.0 (d, 1H), 4.35 (m, 1H), 3.95 (m, 2H), 3.35 (m, 2H), 1.8–0.8 (m, 16H).

Mass Spec: m/z: 274 (M+1H)$^+$, 174[(M+1H)$^+$−100].

What is claimed is:

1. A compound of Formula (1)

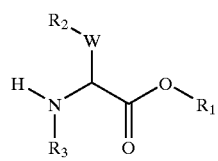

(1)

wherein

W comprises a $C_1$–$C_6$ alkylene group or a direct bond, $R_1$ comprises hydrogen or a $C_1$–$C_6$ alkyl group, $R_2$ comprises
    a 2-thienyl group,
    a 3-thienyl group,
    a 3-benzothiofuranyl group, a 2-tetrahydropyranyl group,
a 3-tetrahydropyranyl group,
a group of the formula

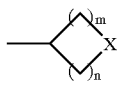

wherein
  n equals 1, 2, 3 or 4,
  m equals 0, 1, or 2,
    wherein n plus m equals 3 or 4; and
  X comprises —S—, or —SO$_2$—; or
a group of the formula

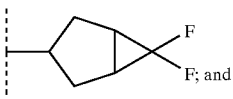

$R_3$ comprises hydrogen or an amino protecting group.

2. A compound of Formula (2)

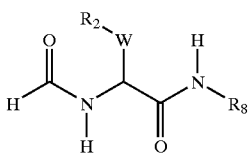

(2)

wherein

W comprises a $C_1$–$C_6$ alkylene group or a direct bond
$R_1$ comprises hydrogen or a $C_1$–$C_6$ alkyl group
$R_2$ comprises
  a 2-thienyl group,
  a 3-thienyl group,
  a 3-benzothiofuranyl group,
  a 2-tetrahydropyranyl group,
  a 3-tetrahydropyranyl group,
  a group of the formula

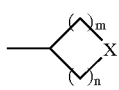

wherein
  n equals 1, 2, 3 or 4,
  m equals 0, 1, or 2,
    wherein n plus m equals 3 or 4; and
  X comprises —S—, or —SO$_2$—; or
a group of the formula

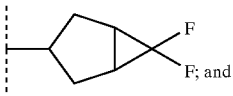

$R_8$ comprises hydrogen or an amino protecting group.

3. A method for preparing a compound of Formula (2)

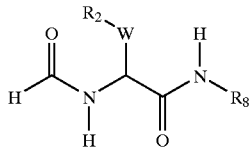

(2)

wherein
  W comprises a $C_1$–$C_6$ alkylene group or a direct bond;
  $R_8$ comprises a $C_1$–$C_6$ alkyl group;
  $R_2$ comprises an alkyl, cycloalkyl, heterocyclyl, aryl, heteroaryl, fused cycloalkylaryl, fused arylcycloalkcyl, fused heterocyclylaryl, fused arylheterocyclyl, fused cycloalkylheteroaryl, fused heteroarylcycloalkyl, fused heterocyclylheteroaryl, or fused heteroarylheterocyclyl group, optionally substituted 1 to 7 times with the following substituents
    a) -hydrogen;
    b) -fluoro;
    c) -chloro;
    d) -bromo;
    e) -iodo;
    f) -cyano;
    g) -nitro;
    h) -perfluoroalkyl;
    i) —T—$R_4$;
    j) -alkyl;
    k) -aryl;
    l) -arylene-alkyl;
    m) —T-alkyl;
    n) —T-alkylene-aryl;
    o) —T-alkylene-arylene-aryl;
    p) —T-alkylene-arylene-alkyl; or
    q) -arylene-T-alkyl;
      wherein T comprises —CH$_2$—, —O—, —N($R_4$)—;
        wherein $R_4$ and $R_5$ independently comprise: -hydrogen, -alkyl, or aryl; and wherein two alkyl group substituents may be taken together to form a fused cycloalkyl ring; and
  wherein the cycloalkyl, heterocyclyl, aryl, heteroaryl, fused cycloalkylaryl, fused arylcycloalkyl, fused heterocyclylaryl, fused arylheterocyclyl, fused cycloalkylheteroaryl, fused heteroarylcycloalkyl, fused heterocyclylheteroaryl, fused heteroarylheterocyclyl, alkylene, and arylene groups in $R_1$, $R_2$, $R_3$, $R_4$, $R_5$, and W may be optionally substituted 1 to 4 times with a substituent group, wherein said substituent group(s) or the term substituted refers to groups comprising:
    a) -hydrogen;
    b) -fluoro;
    c) -chloro;
    d) -bromo;
    e) -iodo;
    f) -cyano;
    g) -nitro;
    h) -perfluoroalkyl;
    i) —Q—$R_6$;
    j) -alkyl; or
    k) -aryl;
      wherein Q comprises: —CH$_2$—, —O—, —N($R_7$)—, wherein $R_6$ and $R_7$ independently comprise: -hydrogen, -alkyl, -aryl, or -alkylene-aryl,
comprising reacting an aldehyde of the formula $R_2$—W—CHO with ammonium formate and a $C_1$–$C_6$ aklkyl isocyanide, wherein $R_2$ and W are defined as in Formula (2).

4. The method of claim 3, wherein $R_2$ comprises a group of the formula

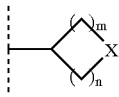

wherein n equals 1, 2, 3 or 4, and m equals 0, 1, or 2, wherein n plus m equals 3 or 4; and X comprises —O—, —N($R_{10}$)—, —S—, or —$SO_2$— wherein $R_{10}$ comprises hydrogen or an amino protecting group.

5. The method of claim 3, wherein $R_2$ comprises a 2-pyridyl, 3-pyridyl, or a 4-pyridyl group.

6. The method of claim 3, wherein $R_2$ comprises a 2-thienyl, 3-thienyl, or 3-benzothiofuranyl group.

7. The method of claim 3, wherein $R_2$ comprises a phenyl group independently substituted 1 to 5 times with a fluoro, chloro, or bromo group.

8. The method of claim 3, wherein $R_2$ comprises a naphthalene group, biphenyl group, or a group of the formula

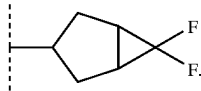

9. The method of claim 3 for producing a compound of Formula (1a) or a strong acid addition salt thereof,

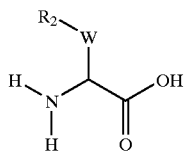

wherein $R_2$ and W are defined as in Formula (2), the method further comprising treating the compound of Formula (2) with a strong acid.

10. The method of claim 9 for producing a compound of Formula (1b)

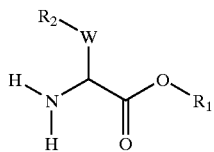

wherein $R_1$ comprises an alkyl group, and $R_2$ and W are defined as in Formula (1a), the method further comprising reacting the carboxyl group of the compound of Formula (1a) with a $C_1$–$C_6$ alkyl alcohol.

11. The method of claim 9 for producing a compound of Formula (1d)

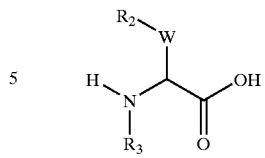

wherein $R_3$ comprises an Fmoc or Boc group, and $R_2$ and W are defined as in Formula (1a), the method further comprising attaching an Fmoc or Boc group.

12. A method of preparing a compound of Formula (1c),

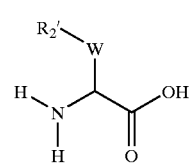

wherein $R_2'$ comprises a 4-piperidinyl group; and

W comprises a $C_1$–$C_6$ alkylene group or a direct bond;

comprising reacting an aldehyde of the formula

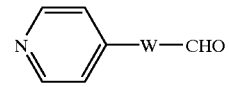

with ammonium formate and a $C_1$–$C_6$ alkyl isocyanide, treating the intermediate product with a strong acid, and reducing the 4-pyridyl group.

13. A method of preparing a compound of Formula (1e)

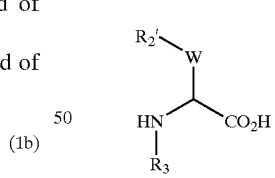

wherein

W comprises a $C_1$–$C_6$ alkylene group or a direct bond;

$R_2'$ comprises a group of the formula

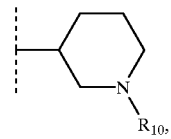

wherein $R_{10}$ comprises a Boc group; and $R_3$ comprises an Fmoc group, comprising
reacting an aldehyde of the formula

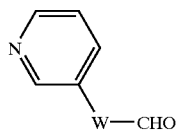

with ammonium formate and a $C_1$–$C_6$ alkyl isocyanide, treating the intermediate product with a strong acid to produce an amino acid or strong acid salt thereof, attaching an Fmoc group to the amino acid or strong acid salt thereof, reducing the 3-pyridyl group, and attaching a Boc group to the secondary amine of the 3-pyridyl group.

14. A method of preparing a compound of Formula (1e)

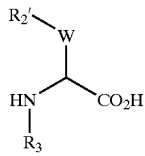

(1e)

wherein

W comprises a $C_1$–$C_6$ alkylene group or a direct bond;

$R_2'$ comprises a group of the formula

and and $R_3$ comprises a Boc group, comprising
reacting an aldehyde of the formula

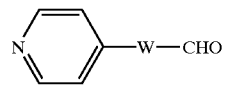

with ammonium formate and a $C_1$–$C_6$ alkyl isocyanide, treating the intermediate product with a strong acid to produce an amino acid or strong acid salt thereof, attaching a Boc group to the amino acid or strong acid salt thereof, and reducing the 4-pyridyl group.

* * * * *